United States Patent
Magnes et al.

(10) Patent No.: US 9,722,281 B2
(45) Date of Patent: *Aug. 1, 2017

(54) PROCESSES FOR PREPARING 1-ALKYL-3-ALKYL-PYRIDINIUM BROMIDE AND USES THEREOF AS ADDITIVES IN ELECTROCHEMICAL CELLS

(71) Applicant: BROMINE COMPOUNDS LTD., Beer Sheva (IL)

(72) Inventors: Ben-Zion Magnes, Meitar (IL); Iris Ben David, Ashdod (IL); Eli Lancry, Ashdod (IL); Mira Bergstein-Freiberg, Omer (IL); Nirit Zer-Zion, Beer-Sheva (IL)

(73) Assignee: BROMINE COMPOUNDS LTD., Be'er-Sheva (IL)

( * ) Notice: Subject to any disclaimer, the term of this patent is extended or adjusted under 35 U.S.C. 154(b) by 0 days.

This patent is subject to a terminal disclaimer.

(21) Appl. No.: 14/765,730

(22) PCT Filed: Feb. 6, 2014

(86) PCT No.: PCT/IL2014/000010
§ 371 (c)(1),
(2) Date: Aug. 4, 2015

(87) PCT Pub. No.: WO2014/122641
PCT Pub. Date: Aug. 14, 2014

(65) Prior Publication Data
US 2015/0372351 A1  Dec. 24, 2015

Related U.S. Application Data

(60) Provisional application No. 61/761,754, filed on Feb. 7, 2013, provisional application No. 61/803,818, filed (Continued)

(51) Int. Cl.
*H01M 10/36* (2010.01)
*H01M 8/18* (2006.01)
(Continued)

(52) U.S. Cl.
CPC ........ *H01M 10/365* (2013.01); *C07D 207/06* (2013.01); *C07D 213/20* (2013.01);
(Continued)

(58) Field of Classification Search
None
See application file for complete search history.

(56) References Cited

U.S. PATENT DOCUMENTS 4,064,324 A    12/1977  Eustace
4,065,601 A *  12/1977  Ajami ................ H01M 12/085
                                                      429/105
(Continued)

FOREIGN PATENT DOCUMENTS

CN    101003510    7/2007
CN    101492423    7/2009
(Continued)

OTHER PUBLICATIONS

Couling et al., "Assessing the factors responsible for ionic liquid toxicity to aquatic organisms via quantitative structure-property relationship modeling," *Green Chemistry*, 2006, vol. 8, pp. 82-90.
(Continued)

*Primary Examiner* — Maria J Laios
(74) *Attorney, Agent, or Firm* — Nixon & Vanderhye P.C.

(57) ABSTRACT

The invention relates to the use of at least one 1-alkyl-3-alkyl-pyridinium halide, in particular 1-alkyl-3-methyl-pyridinium bromide, as an additive in bromine-generating electrochemical cells, such as zinc/bromine cells. Processes for preparing 1-alkyl-3-methyl-pyridinium bromide and concentrated aqueous solutions comprising same for use as additives in the aforementioned cells, are also disclosed.

18 Claims, 3 Drawing Sheets

Figure 1:
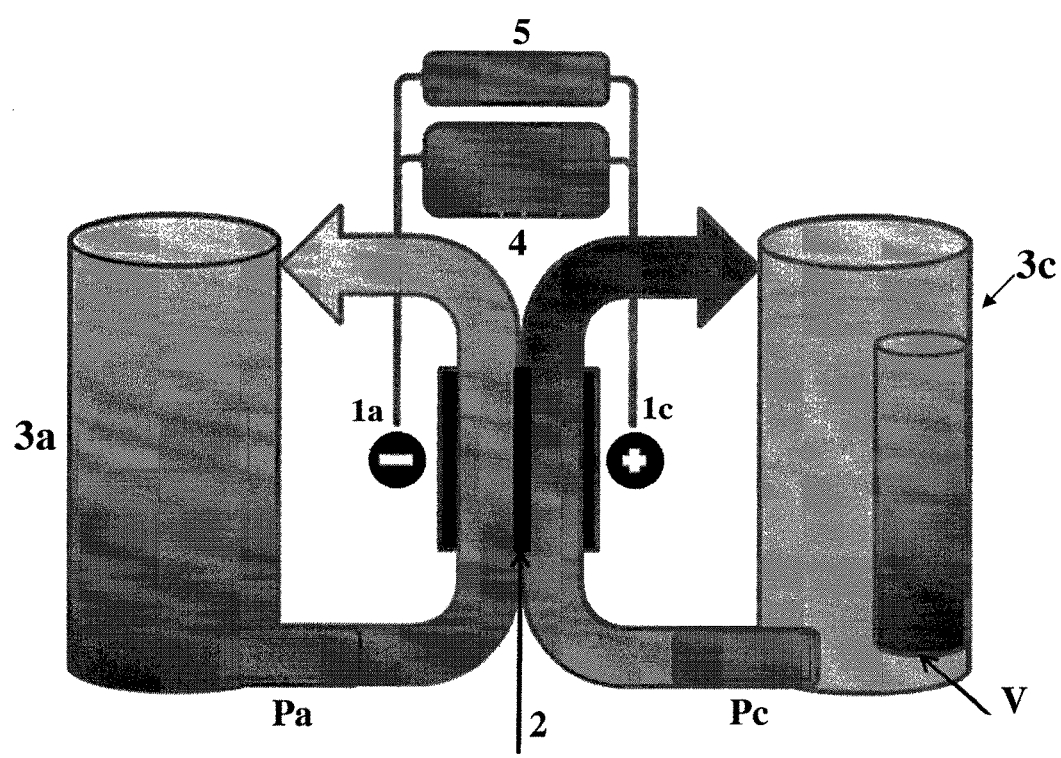

Related U.S. Application Data on Mar. 21, 2013, provisional application No. 61/903,459, filed on Nov. 13, 2013.

(51) Int. Cl.
| | |
|---|---|
| *H01M 8/20* | (2006.01) |
| *H01M 10/42* | (2006.01) |
| *C07D 207/06* | (2006.01) |
| *C07D 213/20* | (2006.01) |
| *H01M 12/08* | (2006.01) |

(52) U.S. Cl.
CPC ............ *H01M 8/188* (2013.01); *H01M 8/20* (2013.01); *H01M 10/4235* (2013.01); *H01M 12/085* (2013.01); *H01M 2300/0002* (2013.01); *Y02E 60/128* (2013.01)

(56) References Cited

U.S. PATENT DOCUMENTS

| | | | |
|---|---|---|---|
| 4,510,218 | A | 4/1985 | Ando et al. |
| 4,520,081 | A | 5/1985 | Höhne et al. |
| 4,631,240 | A | 12/1986 | Walsh |
| 4,906,342 | A * | 3/1990 | Takahashi .............. C25D 3/665 205/233 |
| 5,260,148 | A | 11/1993 | Idota |
| 5,591,538 | A * | 1/1997 | Eidler ................... H01M 4/663 29/623.1 |
| 5,601,943 | A | 2/1997 | Eidler et al. |
| 6,025,457 | A | 2/2000 | Ohno et al. |
| 2001/0028977 | A1 | 10/2001 | Kazacos et al. |
| 2003/0165737 | A1 | 9/2003 | Nakagawa et al. |
| 2011/0233532 | A1* | 9/2011 | Sotzing ..................... C25B 3/00 257/40 |
| 2011/0253553 | A1 | 10/2011 | Bergstein Freiberg et al. |
| 2014/0262818 | A1 | 9/2014 | Ben-David et al. |
| 2014/0302408 | A1 | 10/2014 | Magnes et al. |

FOREIGN PATENT DOCUMENTS

| | | |
|---|---|---|
| CN | 102049202 | 5/2011 |
| EP | 0 404 188 | 12/1990 |
| JP | 11-509035 | 8/1999 |
| WO | WO 2013/042103 | 3/2013 |
| WO | WO 2013/042109 | 3/2013 |
| WO | WO 2013/042110 | 3/2013 |
| WO | WO 2013/168145 | 11/2013 |

OTHER PUBLICATIONS

Docherty et al., "Biodegradability of imidazolium and pyridinium ionic liquids by an activated sludge microbial community," *Biodegradation*, 2007, vol. 18, pp. 481-493.

International Search Report for PCT/IL2014/000010, mailed Jun. 4, 2014, 4 pages.

Written Opinion of the ISA for PCT/IL2014/000010, mailed Jun. 4, 2014, 5 pages.

U.S. Appl. No. 14/210,976, filed Mar. 14, 2014, Magnes et al.

U.S. Appl. No. 14/220,631, filed Mar. 20, 2014, Ben-David et al.

U.S. Appl. No. 14/399,106, filed Nov. 5, 2014, Magnes et al.

Green Chem., vol. 11, 2009, pp. 83-90.

Shao et al., [Pige Huagong], 23, 2006, pp. 23-26.

Hashimoto et al., J. Amer. Cham, Soc, vol. 107, 1985, pp. 4655-4662.

Waterkamp et al., Chem. Eng. & Tech 32 (11), 2009, pp. 1717-1723.

Lukes et al., "Reduction of the Pyridine Nucleus with Formic Acod. III. Reduction of 3-Picoline", Chemicke Listy Pro Vedu a Prumysl, vol. 44, Dec. 31, 1950, pp. 297-300.

Australian Intellectual Property Office, "Patent Examination Report No. 1," issued in connection with Australian Patent Application No. 2014201398, dated Jan. 22, 2016.

Barlet et al; Syntheses et Proprietes D'Halogenures D'Ammonium Quaternaire Utilisables Comme Electrolytes, Journal de Chimie Physique et de Physio-Chimie Biologique, 1984, 81 (5), p. 349-354.

Butler et al., "Zinc/Bromine Batteries," *Advanced Battery Systems*, Chapter 37, pp. 37.1-37.3 (2000).

Cathro et al., "Selection of Quaternary Ammonium Bromides for Use in Zinc/Bromine Cells," *Journal of Power Sources*, vol. 18, pp. 349-370 (1986).

Chinese Office Action issued in App. No. 201280057395.8, dated Sep. 7, 2015 (with English ranslation).

Chinese Office Action issued in App. No. 201380023555.1 dated Mar. 3, 2016 (w/ partial translation.).

Extended European Search Report issued in App. No. 12833458.8 dated Mar. 30, 2015.

International Search Report for PCT/IL2012/000349, mailed Dec. 18, 2012.

International Search Report for PCT/IL2013/000049 mailed Aug. 29, 2013.

Murrill, Halides and Perhalides of the Picolines, Journal of the American Chemical Society, 21, Jun. 19, 1899, p. 828-854.

Nishida et al., "Physical and electrochemical properties of 1-alkyl-3-methylimidazolium tetrafluoroborate for electrolyte," *Journal of Fluorine Chemistry*, 2003, vol. 120, pp. 135-141, Elsevier Science B.V.

Ploquin et al., β-Dicéto énamines hétérocycliques: 2.(Pyridyl-4)-2 indanediones-1,3 C-et N-substituées, Journal of Heterocyclic Chemistry, 17, Jul. 1980; p. 997-1008.

Shlyapnikov, D.S.—Abstract—Khimiya Geterotsiklicheskikh Soedinenii, 1972, (7), p. 966-969.

Shlyapnikov, D.S. Khimiya Geterotsiklicheskikh Soedinenii, 1972, (7), p. 966-969.

Written Opinion of the ISA for PCT/IL2012/000349, mailed Dec. 18, 2012.

Written Opinion of the ISA for PCT/IL2013/000049 mailed Aug. 29, 2013.

* cited by examiner

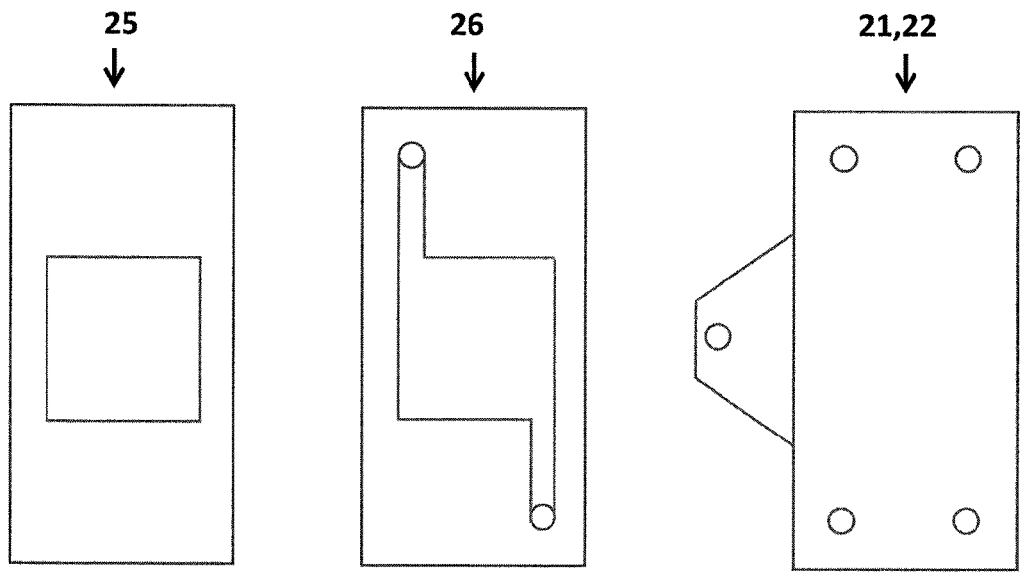

PROCESSES FOR PREPARING 1-ALKYL-3-ALKYL-PYRIDINIUM BROMIDE AND USES THEREOF AS ADDITIVES IN ELECTROCHEMICAL CELLS

This application is the U.S. national phase of International Application No. PCT/IL2014/000010 filed 6 Feb. 2014, which designated the U.S. and claims priority to U.S. Provisional Application Nos. 61/761,754 filed 7 Feb. 2013, 61/803,818 filed 21 Mar. 2013, and 61/903,459 filed 13 Nov. 2013, the entire contents of each of which are hereby incorporated by reference.

The present invention relates to environmentally-friendly processes for preparing 1-alkyl-3-alkyl-pyridinium bromides, allowing the recovery of said compounds in the form of highly concentrated aqueous solutions, which can be used as additives in electrochemical cells.

A synthesis of a series of 1-alkyl-3-methyl-pyridinium halide was recently reported by Sashina et al. [Russian Journal of General Chemistry, vol. 82, No. 12 pp. 1994-1998 (2012)]. The synthesis is based on the alkylation of 3-picoline with the corresponding alkyl halide in toluene as a solvent. Specifically, the preparation of 1-ethyl-3-methyl-pyridinium bromide and 1-butyl-3-methyl-pyridinium bromide is described. The so-formed compounds were tested for their ability to dissolve cellulose. The synthesis of 1-butyl-3-methyl-pyridinium bromide is also described in Green Chem. Vol. 8, p. 82-90 (2006); Biodegradation Vol. 18, p. 481-493 (2007); and Green Chem. Vol. 11, p. 83-90 (2009). The synthesis of 1-ethyl-3-methyl-pyridinium bromide can also be found in a co-assigned patent application PCT/IL2012/000348 [=WO 2013/042109].

There exists a need, in flow cells which involve the generation of elemental bromine, to keep the bromine in a form which can be easily stored and pumped over a broad temperature range. To this end, a bromine-complexing agent, capable of forming a water-immiscible liquid phase upon complexing with elemental bromine, is added to the cell. Thus, the elemental bromine generated during cell charge reacts almost instantaneously with the complexing agent, to form a water-immiscible organic phase. Bromine complexing agents were investigated for trapping elemental bromine in traditional (i.e., membrane-containing) zinc bromine flow batteries. Bromine deactivation in these batteries may be achieved by the use of cyclic quaternary ammonium bromides as complexing agents. In their most general form, these salts are represented by the following formula:

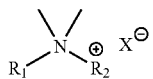

where $R_1$ and $R_2$ indicate the alkyl groups (which are generally different from one another) and X indicates the halide counter ion. It should be particularly noted that in the formula depicted above, the cation is a non-aromatic heterocyclic system. Specifically, N-methyl-N-ethyl pyrrolidinium bromide (abbreviated MEP) and N-methyl-N-ethyl morpholinium bromide (abbreviated MEM) were suggested in U.S. Pat. No. 4,510,218 and are both commercially used for that purpose. N-alkyl pyridinium bromide, such as N-decyl pyridinium bromide and N-dodecyl pyridinium bromide, are also mentioned in U.S. Pat. No. 4,510,218 as additives in zinc-bromine batteries.

U.S. Pat. No. 4,065,601 describes a two-phase electrolyte for use in trapping halogen in conventional zinc/bromine cells, wherein the organic phase of the electrolyte contains water-immiscible organic solvent in combination with a complexing agent which may be selected from the group consisting of quaternary ammonium salts and pyridinium salts.

U.S. Pat. No. 4,064,324 and U.S. Pat. No. 4,631,240 describe the use of some pyridinium salts substituted with acid or ester of the following formula:

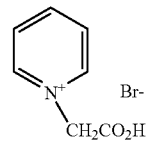

as additives for zinc bromine cell.

Co-assigned international patent application PCT/IL2013/000049 [=WO 2013/168145] discloses that N-alkyl pyridinium halide, 1-alkyl-2-methyl pyridinium halide and 1-alkyl-3-methyl imidazolium halide are useful complexing agents in zinc bromine membraneless flow cells.

Experimental work conducted in support of this invention indicates that 1-alkyl-3-alkyl-pyridinium halide compounds, especially 1-alkyl-3-methyl-pyridinium bromide, are useful as bromine-complexing agents in aqueous solutions of zinc bromide employed in zinc/bromine rechargeable cells, namely, in both membrane-containing and membraneless zinc/bromine flow cells. It has been found that the complex formed by the use of 1-alkyl-3-methyl-pyridinium bromide or mixtures thereof does not solidify at a temperature as low as 0° C. or even −5° C., thus maintaining the flowability of the electrolyte solution at different compositions corresponding to different states of charge of the cell, over a broad operational temperature range. Furthermore, the presence of one or more 1-alkyl-3-methyl-pyridinium bromide compounds in the electrolyte solution minimizes the concentration of 'free' bromine in the aqueous phase under the relevant working conditions. The latter property is believed to be of paramount importance particularly in membraneless zinc/bromine flow cells. While in traditional, membrane-containing zinc/bromine flow cells a concentration of 'free' bromine of up to 1.0 wt % is acceptable (i.e., the concentration of bromine dissolved in the aqueous zinc bromide phase when the cell is fully charged), it is to be noted that in a membraneless configuration the permitted concentration of 'free' bromine is significantly lower than 1.0 wt %. In fact, in the membraneless configuration, it is desirable to minimize the amount of bromine dissolved in the aqueous zinc bromide electrolyte solution. Notably, 1-alkyl-3-methyl-pyridinium bromide compounds are capable of keeping the amount of elemental bromine in the aqueous phase well below 1.0 wt %, e.g., at about 0.1-0.3 wt %, when the cell is fully charged. If higher levels of bromine in the aqueous phase of the electrolyte solution are contemplated, for example, in order to meet the demand in conventional, membrane-containing zinc/bromine flow cells, then the increased levels can be readily achieved upon combining one or more 1-alkyl-3-methyl-pyridinium bromide, optionally with other complexing agents, as set forth below.

In view of the utility of 1-alkyl-3-methyl-pyridinium bromides as additives in the electrolyte of zinc/bromine cells, it may be advantageous to provide said compound directly in the form of a concentrated aqueous solution, which can be readily injected into, and mixed with, the aqueous zinc bromide electrolyte solution circulated in the cell. It has been found that the reaction between 3-picoline and bromoalkanes can be carried out in a "dry" medium, i.e., in a solvent-free reaction mixture, to give the 1-alkyl-3-methyl-pyridinium bromide product in a good yield and purity levels acceptable for the application in zinc/bromine electrochemical flow cells. Thus, the present invention provides processes capable of affording an aqueous concentrate of 1-alkyl-3-methyl-pyridinium bromide in a direct manner, which processes are devoid of the formation, isolation and purification of the compound in a solid state. The term "alkyl", as used herein in connection with 1-alkyl-3-methyl-pyridinium bromide, indicates C1-C10 alkyl group. Preferred are C3-C10 alkyl groups, i.e., $C_nH_{2n+1}$, wherein n is an integer from 3 to 10, especially C3-C8 alkyl groups, which may be either straight-chain or branched. Normal alkyl and branched isoalkyl groups are preferred.

One aspect of the invention relates to a process for preparing an aqueous solution of one or more 1-alkyl-3-methyl-pyridinium bromide, comprising reacting 3-picoline and one or more bromoalkanes in a reaction vessel at a temperature above the melting point of the reaction mixture, in the absence of a solvent, combining the reaction product with water, wherein said reaction product consists essentially of 1-alkyl-3-methyl-pyridinium bromide in a liquid form, and recovering an aqueous solution of said 1-alkyl-3-methyl-pyridinium bromide.

As noted above, the reaction is preferably devoid of a solvent. Most preferably, the process does not involve the formation, isolation and purification of the 1-alkyl-3-methyl-pyridinium bromide in a solid form. Thus, according to the present invention, the solvent-free reaction mixture is heated to a temperature of preferably not less than 70° C., more preferably not less than 80° C., such that the progressively formed 1-alkyl-3-methyl-pyridinium bromide is maintained in a liquid form, providing a stirrable reaction mass. The reaction-derived liquid 1-alkyl-3-methyl-pyridinium bromide is combined directly with water to form a clear aqueous solution.

The reactants, i.e., 3-picoline and the bromalkane, may be used in equimolar amounts. However, it is generally preferred to carry out the reaction with one of the reactants being used in excess. For example, an excess of bromoalkane of up to 20% (molar) can be employed, providing an easily stirrable reaction mixture. However, usually a lower excess of bromoalkane (e.g., in the range from 1 to 5 molar %) is sufficient for running the reaction conveniently.

According to one embodiment of the invention, the process comprises introducing the entire amounts of the reactants into the reaction vessel and then starting and advancing the reaction by slowly heating the reaction mixture in the reactor to about 80° C. However, it is generally more preferred to gradually feed one of the reactants (or both) into the reactor over a prolonged period of time, e.g., of not less than one hour under heating, following which the reactor is maintained for an additional period of time at a temperature that is sufficiently high for preventing solidification of the reaction mass (a "cooking period").

Thus, according to one embodiment of the invention, the process comprises charging a reaction vessel with 3-picoline, heating the reactor, gradually feeding one or more bromoalkanes, preferably in a molar excess of about 1.5 to 3% relative to the 3-picoline, allowing the reaction to reach completion at a temperature above 80° C., to form a reaction mass consisting essentially of 1-alkyl-3-methyl-pyridinium bromide in a liquid form, and combining the liquid reaction mass with water, e.g., de-ionized water, in view of the contemplated utility of the product as an additive for electrochemical cells.

The reaction vessel, which contains 3-picoline, is heated, preferably to a temperature above 70° C., e.g., from 80 to 90° C., following which the gradual addition of the bromoalkane is started and allowed to continue, preferably in a drop-wise manner, for not less than 60 minutes. On an industrial scale, the addition period of the bromoalkane is likely to be not less than 120 minutes. Upon completion of the addition of the bromoalkane, the reaction is maintained under heating at a temperature above 80° C., e.g., from 80° C. to 110° C., for not less that 30 minutes whereby the reaction is completed. Under the conditions set forth above, the reaction mixture, which during the gradual addition of the bromoalkane may consist of two distinct phases, normally progressively transforms into homogeneous reaction mass consisting essentially of 1-alkyl-3-methyl-pyridinium bromide in a liquid form.

The reaction can be carried out under inert atmosphere to prevent side reactions. Such an atmosphere can be provided by inert gases such as nitrogen, argon and the like.

Upon completion of the synthesis stage, residual amounts of the volatile starting materials is removed from the reaction vessel by means of methods known in the art, e.g., evaporation of bromoalkanes, removal under vacuum or addition of water followed by distillation. When the latter option is applied, then the amount of water added is adjusted to serve two useful purposes: the azeotropic distillation and the formation of an aqueous solution of the product. Thus, for example, at the end of the reaction, a first amount of de-ionized water is added to the reaction mixture, followed by cooling and removal of volatile by means of evaporation. A second cycle consisting of water addition and volatile evaporation can be carried out. Finally, if necessary, a small amount of de-ionized water is added to the liquid product, such that the concentration of the 1-alkyl-3-methyl-pyridinium bromide in the solution formed is adjusted within the range from 60 to 90% by weight, and preferably between 70 to 85%. In this way, the product is collected in the form of an aqueous solution, which can be directly applied as an additive for the zinc bromide electrolyte solution.

It should be noted that the synthetic method described above can be employed in order to prepare mixtures consisting of two or more different 1-alkyl-3-methyl-pyridinium bromide compounds. To this end, 3-picoline is reacted with two or more different bromoalkanes in a reaction vessel under the conditions described above, i.e., charging the reaction vessel with 3-picoline, heating the reactor to a temperature of preferably not less than 80° C. and gradually feeding a mixture consisting of two or more bromoalkanes (e.g., in a molar ratio ranging from 5:1 to 1:5) to the reactor. The two bromoalkanes can be added to the reactor simultaneously, either by means of a combined stream or by means of two separate streams, or alternatively, they can be fed consecutively. If the latter method of feeding is applied, then the bromoalkanes are preferably added to the reactor in order of increasing molecular weight, wherein either during or on completion of the addition of the first (lighter) bromoalkane, the temperature of the reaction mixture is increased, such that on addition of the second (heavier) bromoalkane homologoue, the progressively formed mixture of 1-alkyl-3-methyl-pyridinium bromides is maintained in a liquid form, providing an easily stirred reaction mass. At the end of the reaction, the reaction-derived molten mixture consisting of a first 1-alkyl-3-methyl-pyridinium bromide and a second 1-alkyl-3-methyl-pyridinium bromide is combined with de-ionized water (using the same techniques described above in reference to the preparation of an individual 1-alkyl-3-methyl-pyridinium bromide), to form a clear aqueous solution, with product concentration which is preferably not less than 70 weight %.

In its most general form, the process of the invention is illustrated by the following reaction scheme:

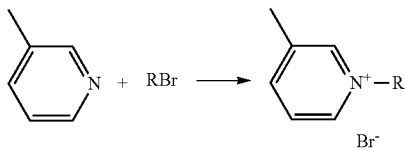

where RBr indicates the bromoalkane which participates in the reaction, e.g., R is selected from the group consisting of C3-C10 normal (straight-chain) or branched alkyl groups. When 1-alkyl-3-methyl-pyridinium bromide with a normal alkyl chain is contemplated, then the corresponding 1-bromoalkanes is employed as a reactant. When R is a branched chain, then the side-chain is preferably methyl or ethyl group and the position of attachment of the bromine is either on the parent chain or on the side chain. An illustrative list of reactants and preferred reaction conditions pertinent to the reaction scheme depicted above are tabulated in Table A ($T_{addition}$ and $t_{addition}$ indicate the temperature during the gradual addition of the bromoalkane and the duration of the addition, respectively; $T_{cooking}$ and $t_{cooking}$ indicate the temperature and duration of the cooking stage which follows the addition of the bromoalkane).

TABLE A

| bromoalkane | $T_{addition}$ (° C.) | $t_{addition}$ (h) | $T_{cooking}$ (° C.) | $t_{cooking}$ (h) |
| --- | --- | --- | --- | --- |
| 1-bromopropane | 80° C. | 3 | 80° C. | 1.5 |
| 1-bromobutane | 79° C. | 4 | 80° C. | 0.5 |
| 1-bromopentane | 80° C. | 2 | 82-84° C. | 2.5 |
| 1-bromohexane | 80° C. | 3 | 87-90° C. | 2.5 |
| 1-bromo-2-methylpropane | 80° C. | 3.5 | 100° C. | 21 |
| 3-(bromomethyl)heptane | 80° C. | 1.5 | 100-105° C. | 26 |
| 1-bromoethane | 80° C. | 1.5 | 90° C. | 1.25 |
| 1-bromobutane (consecutive addition) | 87° C. | 4 | | |
| 1-bromoethane 1-bromobutane (simultaneous addition) | 85° C. | 3.5 | 88-90° C. | 3 |

The melting points of the products are typically below 100° C., such that the solvent-free reaction according to the invention can be conducted under fairly reasonable conditions. Furthermore, the bromoalkanes identified in Table A are all liquids at room temperature, and can be easily fed to the reaction vessel. However, when 1-methyl-3-methyl pyridinium bromide is contemplated, then the bromomethane reactant (which is a gas) is most conveniently supplied to the reaction by means of in-situ generation, and is combined with the 3-picoline in the presence of a solvent or a mixture of solvents, i.e., a mixture of de-ionized water and water miscible solvent such as lower alkanol and acetonitrile. Thus, the invention provides a process comprising charging a reaction vessel with 3-picoline and a solvent, or a solvent mixture, in-situ producing and feeding bromomethane (e.g., by a reaction between sulfur hexabromide $SBr_6$ and methanol) to said reaction mixture, e.g., through a deep tube at a temperature of 10-35° C., removing volatile materials and collecting 1,3-dimethyl pyridinium bromide in the form of a concentrated aqueous solution.

The concentrated aqueous solutions formed by the processes described above form another aspect of the invention. Thus, the invention relates also to a concentrated aqueous solution of one or more 1-alkyl-3-methyl pyridinium bromide, with the concentration of the solution being from 60 wt % to 90 wt %, more preferably from 70 wt % to 85 wt %. The aqueous solutions provided by the present invention are clear and characterized in that they contain 1-alkyl-3-methyl pyridinium bromide which was "isolated in a non-solid form". By the term "isolated in a non-solid form" is meant that the 1-alkyl-3-methyl pyridinium bromide was not prepared in a solid (e.g., crystalline) form, and was neither converted into, nor stored in, a solid form. The aqueous solution of the invention may contain 1-alkyl-3-methyl pyridinium bromide in an individual form or in the form of mixtures, e.g., binary mixtures in which the molar ratio between the two different 1-alkyl-3-methyl pyridinium bromide is preferably from 1:5 to 5:1, e.g., from 1:4 to 4:1 and more specifically, from 1:3 to 3:1.

It should be noted that some of the 1-alkyl-3-methyl-pyridinium bromides described herein are believed to be novel. Thus, 1-alkyl-3-methyl-pyridinium bromide wherein the alkyl group at position 1 contains an odd number of carbon atoms, for example, 1-methyl-3-methyl-pyridinium bromide, 1-propyl-3-methyl-pyridinium bromide (e.g., n-propyl) and 1-pentyl-3-methyl-pyridinium bromide (e.g., n-pentyl), forms another aspect of the invention. Furthermore, the sub-class consisting of 1-alkyl-3-methyl-pyridinium bromides wherein the alkyl group at position 1 is a branched chain containing not less than four carbon atoms with a side-chain which is either methyl or ethyl group, for example, 1-iso-butyl-3-methyl-pyridinium bromide and 1-iso-octyl-3-methyl-pyridinium bromide is also believed to be novel and forms another aspect of the invention.

In another aspect, the invention relates to the use of 1-alkyl-3-alkyl-pyridinium halide, especially 1-alkyl-3-methyl-pyridinium halide (e.g., bromide), as an additive for electrochemical cells which are based on the generation of elemental bromine (bromine-generating electrochemical cells), for example, zinc bromine membraneless flow cell.

In another aspect, the invention provides an electrolyte solution suitable for use in electrochemical cells which are based on the generation of elemental bromine (bromine-generating electrochemical cells), for example, zinc bromine membraneless flow cell, said electrolyte solution comprising aqueous bromide (e.g., aqueous zinc bromide solution), and a liquid complex composed of 1-alkyl-3-alkyl-pyridinium halide, especially 1-alkyl-3-methyl-pyridinium halide (e.g., bromide), combined with one or more bromine molecules.

In yet another aspect, the invention is directed to a method of operating a bromine-generating electrochemical cell, for example, zinc bromine flow cell, such as zinc bromine membraneless flow cell, comprising adding to the electrolyte of said cell at least one 1-alkyl-3-alkyl pyridinium halide, especially 1-alkyl-3-methyl-pyridinium halide (e.g., bromide); and charging and/or discharging said cell.

The 1-alkyl-3-methyl-pyridinium bromide can be added to the zinc bromide solution in any suitable form, e.g., as a solid or as a clear aqueous solution prepared as set forth above, which solution can be conveniently injected into the electrolyte circulating in an energy storage device based on zinc/bromine flow cells. A suitable aqueous electrolyte solution which may be used in zinc bromine batteries has the following composition: $ZnBr_2$ at a concentration from 0.5 M to 5.0 M, (preferably 1.0 to 3.0 M, e.g., from 2.0 to 3.0 M);

a complexing agent at a concentration of not less than 0.25 M, e.g., from 0.25 M-2.5 M and optionally, one or more water soluble salts such as halide salts, e.g., zinc chloride, sodium chloride or potassium chloride, and also sulfate salts (both are conductivity enhancers up to 3M). The total concentration of these secondary water-soluble salts, which may be optionally present in the electrolyte solution, can be up to 3.5 M, e.g., between 0.5-3.5 M. It is noted that the electrolyte further comprises added bromine or in-situ chemically generated bromine, and also the electrochemically generated bromine (which is formed in-situ in the cell on charging). On charging, the zinc bromide is consumed and bromine is generated. On discharging, the aqueous phase of the electrolyte is again concentrated with respect to $ZnBr_2$, and the concentration of elemental bromine is decreased.

The preferred 1-alkyl-3-methyl-pyridinium bromides utilizable according to the invention have alkyl group attached at position 1 of the pyridine ring selected from the group consisting of propyl (e.g., n-propyl), butyl (e.g., n-butyl), pentyl (e.g., n-pentyl) and hexyl (e.g., n-hexyl). 1-n-butyl-3-methyl-pyridinium bromide (abbreviated herein 3-MBPy) has emerged from the experimental work conducted in support of the invention as an especially useful additive for zinc bromide electrolyte solution, either alone or in combination with other 1-alkyl-3-methyl-pyridinium bromides, such as 1-n-propyl-3-methyl-pyridinium bromide (abbreviated herein 3-MPrPy), 1-n-pentyl-3-methyl-pyridinium bromide (abbreviated herein 3-MPePy) and 1-n-hexyl-3-methyl-pyridinium bromide (abbreviated herein 3-MHePy).

Moreover, the one or more 1-alkyl-3-methyl-pyridinium bromides can be also combined in the zinc bromide electrolyte solution together with complexing agents belonging to other classes, especially compounds represented by Formulas I, II and III:

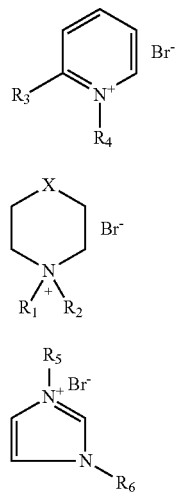

Formula (I)

Formula (II)

(Formula (III))

In Formula (I), $R_3$ is hydrogen or alkyl (especially methyl) and $R_4$ is independently an alkyl group, preferably ethyl.

In Formula (II), X is null (i.e, a five-membered pyrrolidinum system), —$CH_2$— or —O— (i.e. six-membered piperidinum and morpholinium systems, respectively), and $R_1$ and $R_2$ are independently alkyl groups, with at least one of $R^1$ and $R^2$ being an alkyl group comprising not less than three carbon atoms, preferably not less than four carbon atoms; preferably $R_1$ is methyl and $R_2$ is preferably C4-C10 straight-chain or branched alkyl group.

In Formula (III), $R_5$ is an alkyl group (especially methyl) and $R_6$ is independently an alkyl group, preferably C3-C10 straight-chain or branched alkyl group.

For example, 1-alkyl-3-methyl-pyridinium bromides, such as 1-n-butyl-3-methyl-pyridinium bromide, can be combined with one or more of the following compounds:

Compounds of Formula (I), selected from the group consisting of:

alkyl pyridinium bromide (where $R_3$=H and $R_4$=alkyl; e.g., N-ethyl pyridinium bromide, abbreviated herein EPy); and 1-alkyl-2-methyl pyridinium bromide (where $R_3$=methyl and $R_4$=alkyl; e.g., 1-ethyl-2-methyl pyridinium bromide, abbreviated herein 2-MEPy).

Compounds of Formula (II), selected from the group consisting of:

N-methyl-N-alkyl pyrrolidinium bromide (where X is null, $R_1$=methyl and $R_2$ is C4-C10 alkyl; e.g., N-methyl-N-butyl pyrrolidinium bromide, abbreviated herein MBP, N-methyl-N-hexyl pyrrolidinium bromide, abbreviated herein MHeP, N-methyl-N-isooctyl pyrrolidinium bromide, abbreviated herein MiOP); and N-methyl-N-alkyl morpholinium bromide (where X is —O—, $R_1$=methyl and $R_2$ is C4-C10 alkyl; e.g., N-methyl-N-hexyl morpholinium bromide, abbreviated herein MHeM).

Compounds of Formula (III), selected from the group consisting of 1-alkyl-3-methyl imidazolium bromide, e.g., 1-n-butyl-3-methyl imidazolium bromide.

Regarding the compounds of Formula (I) which are N-alkyl pyridinium bromide, it is noted that said compounds can be readily prepared by methods known in the art. For example, N-ethyl pyridinium bromide can be synthesized by a reaction of pyridine with bromoethane, as described by Shao et al. [Pige Huagong, 23(1), p. 23-26 (2006)] and by Hashimoto et al. [J. Amer. Chem. Soc., 107(16), (1985), p. 4655-4662 (1985)]. Regarding the compound of Formula (I) which is 1-alkyl-2-alkyl pyridinium bromide, it is noted that a complexing agent suitable for use according to the invention is 1-ethyl-2-methyl pyridinium bromide, which is prepared by reacting 2-picoline with ethyl bromide, as illustrated by the following reaction scheme:

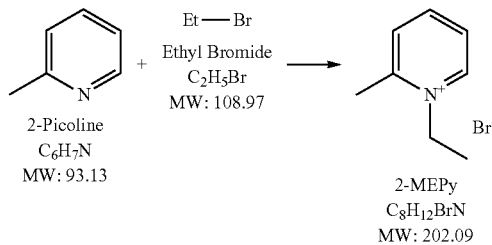

The reaction is carried out by charging a pressure reactor with the reactants and optionally also with a solvent, which may be either an aqueous or organic solvent. Alternatively, ethyl bromide can be used in excess. It is possible to introduce the entire amounts of the reactants into the reactor and then start the reaction by heating the reaction mixture. However, it is also possible to gradually feed one or more of the reactants (e.g., the ethyl bromide) into the reactor over a period of not less than one hour under heating. The reaction mixture is heated, preferably to a temperature of not less than 90° C., and the reaction is allowed to proceed under pressure for a few hours. For example, the pressure reactor, which contains 2-picoline, is heated, preferably to a temperature above 70° C., e.g., from 80 to 110° C., following which the gradual addition of the ethyl bromide is started and allowed to continue, preferably in a continuous manner, for not less than 60 minutes. Upon completion of the addition of ethyl bromide, the reaction is maintained under heating at a temperature above 95° C., e.g., from 95 to 110° C., for not less than 30 minutes whereby the reaction is completed. The product is conveniently collected in the form of an aqueous solution, which can be directly applied as an additive for the electrolyte solution in accordance with the present invention. To this end, upon completion of the reaction, the organic solvent and/or residual amounts of the starting materials are removed from the reaction vessel by means of methods known in the art, e.g., distillation. Water (de-ionized water) can then be added into the reactor, before the product has solidified, to afford the complexing agent in an aqueous form. Preparative procedures are also set forth below.

Regarding the compounds of Formula (II), in which X is null (pyrrolidinium system) and $R^1$ and $R^2$ indicate C1-C3 alkyl and C4-C10 alkyl, respectively, with said C4-C10 alkyl group being either linear or branched, it is noted that these compounds can be synthesized by the reaction of $R^1$-substituted pyrrolidine with $R^2Br$, either in an organic solvent such as acetonitrile or in the absence of a solvent. If a solvent is used, then the reaction vessel is charged with that solvent and the $R^1$-substituted pyrrolidine starting material, following which the $R^2Br$ reactant is added gradually under heating. On completion of the addition of the alkyl bromide $R^2Br$, the reaction mixture is kept under heating at a temperature of not less than 80° C. for a few hours. At the end of the reaction, the solvent is removed and the product can be recovered in the form of a concentrated aqueous solution by the addition of deionized water, such that the resultant aqueous concentrate can be directly applied as an additive in the electrochemical cell. In the absence of a solvent, then the reaction vessel is charged with the two reactants and the reaction mixture is gradually heated, e.g. during at least one hour, arriving at a reaction temperature which is preferably not less than 90° C. A stirrable reaction mixture is formed, which is maintained at said elevated temperature for a few hours, allowing the reaction to reach completion. The product is recoverable in the form of a concentrated aqueous solution as set out above. Preparative procedures are also set forth below.

Regarding the class of 1-alkyl-3-alkyl imidazolium bromide compounds of Formula (III), a preferred complexing agent suitable for use according to the invention is 1-n-butyl-3-methyl imidazolium bromide:

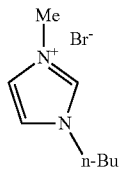

which can be readily synthesized by methods known in the art. In general, 1-alkyl 3-methyl imidazolium halide can be prepared by reacting 1-methylimidazole with alkyl halide. For example, the synthesis of 1-alkyl 3-methyl imidazolium bromide is described in CN 101492423, CN 101003510 and by Waterkamp et al. [Chemical Engineering & Technology 32(11), p. 1717-1723 (2009)]. The compound is also commercially available.

As noted above, the bromine complexing agents of the invention may be used either in individual form or in the form of mixtures, e.g., binary mixtures, in which the molar ratio between the two components of the mixture is from 1:5 to 5:1. Preferred combinations include 1-n-butyl-3-methyl pyridinium bromide together with at least one of N-ethyl pyridinium bromide, 1-ethyl-2-methyl pyridinium bromide and 1-ethyl-3-methyl pyridinium bromide. The experimental results reported below show that 1-n-butyl-3-methyl pyridinium bromide and combinations thereof with additional complexing agents do not undergo solidification even at a temperature as low as −5° C., the amount of bromine measured in the aqueous phase is very low and the electrolyte solution exhibits good conductivity and low viscosity, with the aqueous and organic phases being mutually immiscible, exhibiting two separate phases.

Structures of zinc/bromine batteries which can employ the electrolyte of the invention are known in the art and are described, for example, in U.S. Pat. No. 4,510,218 and WO 2013/042103. FIG. 1 provides a schematic illustration of an example of a traditional, membrane-containing zinc-bromine cell, wherein numerals 1a and 1c indicate the anode and cathode, respectively, and numeral 2 represents the separator positioned between the electrodes. A reservoir for accommodating an aqueous solution of zinc bromide, used as the anolyte, is indicated by numeral 3a. Similarly, a reservoir 3c contains the catholyte, which consists of two liquid phases: an upper, aqueous solution of zinc bromide and a lower, dense organic phase comprising the elemental bromine in a form of a complex. The flow paths allowing the circulation of the anolyte and catholyte are respectively indicated by arrows (the streams are driven by pumps Pa, Pc). A suitable valve (v) allows injection of bromine into the flow path of the catholyte on discharge only. A power source and a load are electrically connected to the electrodes (numerals 4 and 5, respectively).

The operation of the cell shown in FIG. 1 is now described in more detail. The electrolyte used in the cell is an aqueous solution of zinc bromide, which is generally fed to the two compartments of the cell from two separate external reservoirs, utilizing a suitable circulation system. The term "anode" is used herein to indicate the electrode where metal zinc is formed (during charge) and oxidized (during discharge). The term "cathode" is used herein to indicate the electrode where elemental bromine evolves (during charge) and reduced (during discharge).

During charge, an electric current is supplied to the cell from an external source, causing the deposition of zinc metal onto the anode and the concurrent generation of elemental bromine at the cathode, as shown by the following reaction:

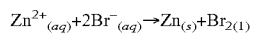

The aqueous electrolyte solution which circulates through the cathodic side during the cell charge contains the complexing agent which is capable of readily forming a water-immiscible liquid phase upon complexing with elemental bromine. The dense bromine-containing oily phase tends to settle at the bottom of the reservoir used for holding the catholyte. The recirculation of the bromine-containing medium is prevented using suitable mechanical means, thus allowing the accumulation of elemental bromine in the catholyte reservoir. In this way, bromine is produced and stored in a reservoir outside the electrode.

During discharge, the reverse chemical reaction takes place and an electric current is drawn from the cell. The bromine-containing liquid, which forms part of the catholyte, is brought to the cathodic side of the cell, while the anolyte is simultaneously circulated through the anodic side. This results in the dissolution of the zinc anode to give zinc ions and the reduction of elemental bromine to form bromide ions (and the generation of electrical current). The chemical reaction is represented by the following equation:

$$Zn_{(s)}+Br_{2(l)} \rightarrow Zn^{2+}_{(aq)}+2Br^-_{(aq)}$$

The use of a separator in a traditional zinc bromine flow cell utilizing different anolyte and catholyte solutions is for the purpose of preventing the mixing of the solutions and the migration of elemental bromine molecules to the anolyte stream. It should be noted that bromine migration to the anodic side results in a lower columbic efficiency due to direct chemical reaction between the elemental bromine and the zinc anode ("self discharge"). The separator is usually a microporous plastic sheet or an ion exchange membrane (for example Nafion®) that acts as a physical barrier for different electrolyte solutions or specific species contained in those solutions or produced and consumed during the cell operation. Still, in order to maintain electrical conductivity and charge neutralization, the separator must allow the transport of required ions from one compartment to the other.

However, one serious disadvantage associated with the use of a separator in a zinc-bromine flow cell is that the cell internal resistance is inevitably increased. The latter is a limiting factor in terms of the ability of the electrochemical system to deliver high currents with minimal voltage drop.

It may therefore be appreciated that the use of membraneless configuration can be highly beneficial. In its most general form, a membraneless electrochemical cell configuration comprises a pair of electrodes and is devoid of a physical barrier (i.e., a separator) in the reaction zone between the electrodes. By removing the separator, several advantages can be gained. First, the internal resistance which is developed due to the physical barrier for ions movement from one compartment to the other is eliminated. Second, in a membraneless electrochemical cell, one electrolyte storage tank and one pump for circulating said electrolyte are sufficient, which is certainly more cost effective in comparison with the operation of the common zinc-bromine flow cell illustrated in FIG. 1, in which two electrolyte tanks and two pumps are necessary.

Another aspect of the invention relates to the use of a compound of Formula (II) wherein X is null and $R_1$ is methyl, i.e., a compound of Formula (IIA):

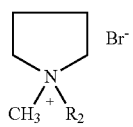

Formula (IIA)

wherein $R_2$ is C4-C8 straight-chain or branched alkyl group, as an additive for electrochemical cells which are based on the generation of elemental bromine, for example, zinc bromine membraneless flow cell. An electrolyte solution comprising aqueous zinc bromide solution, and a liquid complex composed of a compound of Formula II(A), combined with one or more bromine molecules, forms another aspect of the invention. In yet another aspect, the invention is directed to a method for operating a zinc bromine flow cell, for example, zinc bromine membraneless flow cell, comprising adding to the electrolyte of said cell at least one compound of Formula (IIA), and charging and/or discharging said cell. The preferred compounds of Formula (IIA) are selected from the group consisting of N-methyl-N-n-butyl pyrrolidinium bromide and N-methyl-N-isooctyl pyrrolidinium bromide.

The experimental results reported below indicate that compounds of Formula (IIA) display better activity in comparison with the conventional methyl ethyl pyrrolidinium bromide. The compounds of Formula (IIA) may be used either in individual form or in the form of mixtures, e.g., binary mixtures, in which the molar ratio between the two components of the mixture is from 1:5 to 5:1. For example, such mixtures may include a compound of Formulas (I) or (III), e. g., 1-butyl-3-methyl-imidazolium bromide, in combination with the compound of Formula (IIA).

Compounds of Formula (IIA) can be prepared by the methods set forth above in respect of the compounds of Formula (II). Furthermore, the compounds of Formula (IIA) such as N-methyl-N-isooctyl pyrrolidinium bromide are believed to be novel and form a further aspect of the invention.

EXAMPLES

Example 1

Preparation of 1,3-Dimethylpyridinium bromide (3-MMPy)

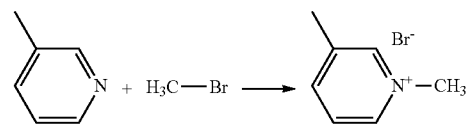

A three neck round bottom flask (1 L) was equipped with a magnetic stirrer, a thermocouple well, a dip tube connected to a methyl bromide generator (from $SBr_6$ and methanol) and a condenser assembled with methyl bromide absorbing system. The flask was charged with 3-picoline (311 g), acetonitrile (207 g) and DIW (81 mL). The reaction mixture was cooled in an ice bath and bromomethane (gas) was fed during 1.6 hours. The volatiles were removed by rotavapor and the residue was diluted with small volume of DIW. Final product, 558.4 g, 87.9 weight % (argentometric titration); yield, 84%.

Example 2

Preparation of 1-n-propyl-3-methyl-pyridinium bromide (3-MPrPy)

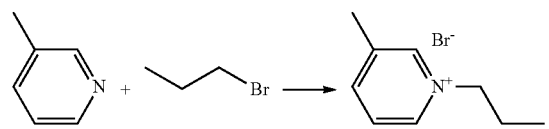

A double surface reactor (1 L) was equipped with a mechanical stirrer, a condenser, a thermocouple well and a dropping funnel. The reactor was purged with nitrogen during the whole procedure. The reactor was charged with 3-picoline (372 g) and heated to 80° C. 1-Bromopropane (500 g) was added drop-wise during 3 hours. The reaction mixture was heated at 80° C. for 1.5 hours. DIW (500 mL) was added; the mixture was cooled and the volatiles were evaporated (rotavapor, 400 mL distillate).

Another 500 mL DIW was added and the mixture was re-evaporated (550 mL distillate). Finally, the mixture was diluted with small volume of DIW. Final product, 1137 g, 73.1 weight % (argentometric titration); yield, 96%.

Example 3

Preparation of 1-n-butyl-3-methyl pyridinium bromide (3-MBPy)

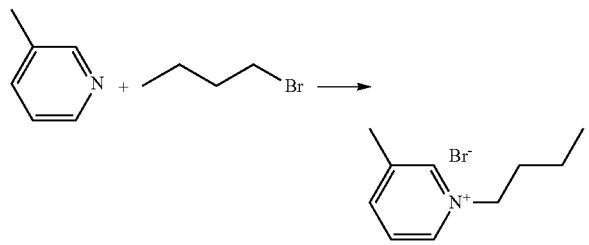

A double surface reactor was equipped with a mechanical stirrer, a condenser, a thermocouple well and a dropping funnel. The reactor was purged with nitrogen during the whole procedure. The reactor was charged with 3-picoline (465 g) and heated to 79° C. n-Butyl bromide (718 g) was then added drop-wise during 4 hours. The reaction mixture was heated at 80° C. for 0.5 hours. DIW (500 mL) was added, the mixture was cooled and the volatiles evaporated in a rotavapor. Additional DIW (500 g) was added and the mixture was re-evaporated. DIW was added to correct dilution. Final product, 1431 g, 77.5 weight % (argentometric titration); yield, 96.5%.

Example 4

Preparation of 1-n-pentyl-3-methyl-pyridinium bromide (3-MPePy)

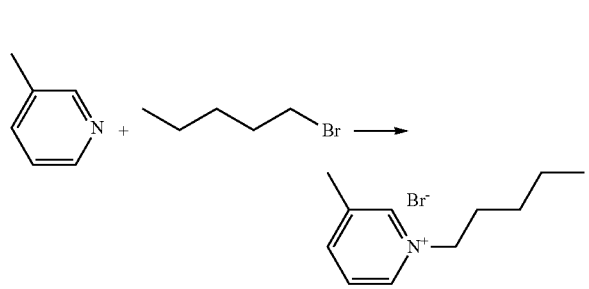

A double surface reactor (1 L) was equipped with a mechanical stirrer, a condenser, a thermocouple well and a dropping funnel. The reactor was purged with nitrogen during the whole procedure. The reactor was charged with 3-picoline (370.5 g) and heated to 80° C. 1-Bromopentane (610 g) was added drop-wise during 2 hours. The reaction mixture was heated at 82-84° C. for 2.5 hours. DIW (500 mL) was added; the mixture was cooled and the volatiles were evaporated (rotavapor). Another 500 mL DIW was added and the mixture was re-evaporated. Finally, the mixture was diluted with small volume of DIW. Final product, 1115 g, 82.7 weight % (argentometric titration); yield, 95%.

Example 5

Preparation of 1-n-hexyl-3-methyl-pyridinium bromide (3-MHePy)

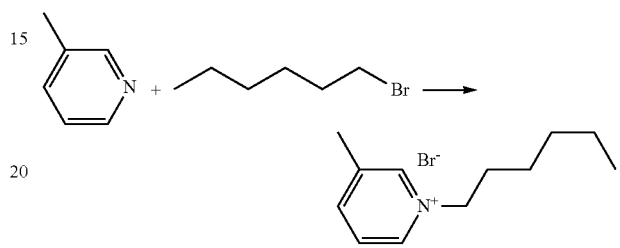

A four neck round bottom flask (500 mL) was equipped with a mechanical stirrer, a condenser, a thermocouple well and a dropping funnel. The flask was purged with nitrogen during the whole procedure. The flask was charged with 3-picoline (83 g) and heated to 80° C. 1-Bromohexane (150 g) was added drop-wise during 3 hours. The reaction mixture was heated at 87-90° C. for 2.5 hours. DIW (100 mL) was added; the mixture was cooled and the volatiles were evaporated (rotavapor). Another 100 mL DIW was added and the mixture was re-evaporated. Finally, the mixture was diluted with small volume of DIW. Final product, 292 g, 77.1 weight % (argentometric titration); yield, 98%.

Example 6

Preparation of 1-iso-butyl-3-Methyl-pyridinium bromide (3-MiBuPy)

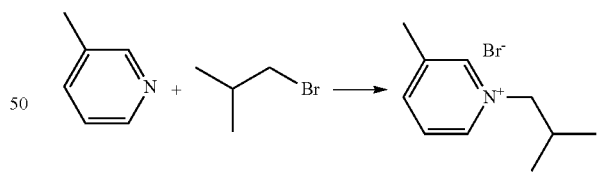

A double surface reactor (1 L) was equipped with a mechanical stirrer, a condenser, a thermocouple well and a dropping funnel. The reactor was purged with nitrogen during the whole procedure. The reactor was charged with 3-picoline (422.7 g) and heated to 80° C. 1-Bromo-2-methylpropane (630 g) was added drop-wise during 3.5 hours. The reaction mixture was heated at 100° C. for 21 hours. DIW (200 mL) was added; the mixture was cooled and the volatiles were evaporated (rotavapor). Another 500 mL DIW was added and the mixture was re-evaporated (510 mL distillate). Finally, the mixture was diluted with small volume of DIW. Final product, 1226 g, 74.1 weight % (argentometric titration); yield, 87%.

Example 7

Preparation of 1-iso-octyl-3-Methyl-pyridinium bromide (3-MiOcPy)

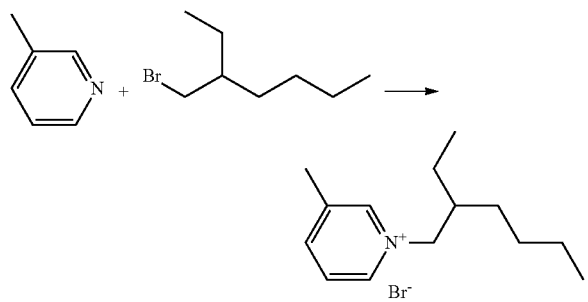

A double surface reactor (1 L) was equipped with a mechanical stirrer, a condenser, a thermocouple well and a dropping funnel. The reactor was purged with nitrogen during the whole procedure. The reactor was charged with 3-picoline (237 g) and heated to 80° C. 3-(Bromomethyl) heptane (500 g) was added drop-wise during 1.5 hours. The reaction mixture was heated at 100-105° C. for 26 hours. DIW (300 mL) was added; the mixture was cooled and the volatiles were evaporated (rotavapor, 325 g distillate). Another 300 mL DIW was added and the mixture was re-evaporated (450 g distillate). Finally, the mixture was diluted with small volume of DIW. Final product, 864 g, 65 weight % (argentometric titration); yield, 77%.

Example 8

Preparation of a mixture of 1-ethyl-3-methyl-pyridinium bromide and 1-n-butyl-3-methyl-pyridinium bromide (1:3)

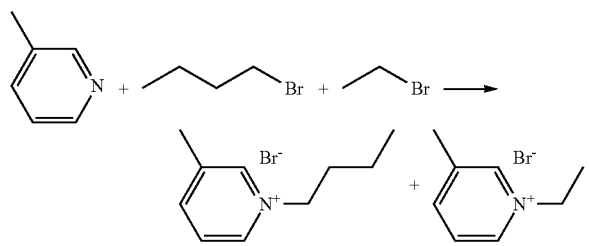

A double surface reactor (1 L) was equipped with a mechanical stirrer, a condenser, a thermocouple well and a dropping funnel. The reactor was purged with nitrogen during the whole procedure. The reactor was charged with 3-picoline (465.6 g) and 1-bromoethane (136.2 g). The reaction mixture was gradually heated to 87° C. during 1.3 hours. 1-Bromobutane (520.7 g) was added drop-wise during 4 hours. The mixture was further heated at 90° C. for 1.25 hours. DIW (754 mL) was added; the mixture was cooled and the volatiles were evaporated (rotavapor). Finally, the mixture was diluted with small volume of DIW. Final product, 1367 g, 79.7 weight % (argentometric titration); yield, 97.7%.

Example 9

Preparation of a mixture of 1-ethyl-3-methyl pyridinium bromide and 1-n-butyl-3-methyl-pyridinium bromide (1:3)

A double surface reactor (1 L) was equipped with a mechanical stirrer, a condenser, a thermocouple well and a dropping funnel. The reactor was purged with nitrogen during the whole procedure. The dropping funnel was charged with a mixture of 1-bromoethane (136.2 g) and 1-bromobutane (520.7 g) and the reactor was charged with 3-picoline (465.6 g). The reactor was heated to 85° C. and the alkyl bromide mixture was added drop-wise via dip tube during 3.5 hours. The mixture was further heated at 88-90° C. for 3 hours. DIW (550 mL) was added; the mixture was cooled and the volatiles were evaporated (rotavapor). Finally, the mixture was diluted with small volume of DIW. Final product, 1367 g, 79.7 weight % (argentometric titration); yield, 97.7%.

Examples 10-19

Zinc bromide electrolyte Solutions which Contain 1-alkyl-3-methyl pyridinium bromide In the next set of Examples, zinc bromide electrolyte solutions were prepared and tested, in order to demonstrate the ability of 1-alkyl-3-methyl pyridinium bromide compounds, either alone or in combinations with additional complexing agents, to form bromine-containing complexes in such solutions. To this end, 24 ml samples were prepared, with electrolyte compositions corresponding to distinct states of charge (SOC) defined by the concentrations of zinc bromide and elemental bromine. Each sample contains, in addition to the aqueous solution of zinc bromide and elemental bromine (which were present in the sample in suitable amounts as tabulated below, in order to match the state of charge investigated), also zinc chloride at a concentration of up to 0.5M and optionally potassium chloride at 1.0M concentration. The samples were stored at 25° C. for 24-hours after preparation before any measurement was conducted. One or more following properties of the samples were determined: the temperature at which a solid phase is formed in the electrolyte, free bromine concentration in the aqueous phase, solution conductivity and viscosity of the aqueous and organic phases, using the following methods:

1) The specific conductivity of the zinc bromide solutions containing the complexing agents was measured at room temperature after the addition of bromine to the samples using InnoLab 740 instrument with graphite conductivity cell.
2) The temperature at which the formation of a solid phase takes place in the electrolyte solution was determined by gradually cooling the samples from room temperature (RT, approximately 25° C.) to −5° C. The cooling regime was as follows: the temperature was decreased from RT down to 15° C. with a cooling rate of 0.2° C./min, and kept at 15° C. for 4 hours and so forth down to −5° C. At each of the following temperatures: 15° C., 10° C., 5° C., 0° C. and −5°

C., the solution was maintained at a constant temperature for four hours. The cooling test was performed in polyethylene glycol solution, until the formation of crystals was observed.

3) The bromine concentration in the aqueous phase above the polybromide complex-oily phase was determined by a conventional iodometric titration technique. Each vial was sampled two times at room temperature.

4) The electrolyte solution was allowed to stand for 24 hours at 25° C. and then separated into aqueous and organic phases in a separating funnel for 2 hours at 25° C. The density of each phase was measured. Viscosity measurements were done with Zeitfuchs cross-arm viscometer and/or Cannon-Fenske opaque viscometer.

In view of the fact that the composition of an electrolyte solution varies while the charge process is in progress (the amount of zinc bromide decreases while the amount of elemental bromine correspondingly increases), the utility of the additives under consideration was tested at different compositions which match different states of charge. In the experiments, the composition of the electrolyte solutions was adjusted to correspond to the beginning, middle and end of charge process (SOC of 0%, 50 and 100%, respectively). The letters A, B and C next to the Example's number indicate these three SOC that were investigated, respectively.

In the first sub-set of Examples, different 1-alkyl-3-methyl-pyridinium bromides were tested separately as complexing agents for zinc/bromine cells. The results are tabulated in Table 1 (con. is the abbreviation for conductivity).

TABLE 1

| Ex. | % SOC | $ZnBr_2$(M) | $Br_2$, M | additive | [additive] [M] | Physical state of polybromide complex | % $Br_2$, aq. | Con., mS/cm |
|---|---|---|---|---|---|---|---|---|
| 10A | 0 | 2.25 | 0.2 | 3-MPrPy | 0.8M | Liquid at 0° C. | 0.10 | 128 |
| 10B | 50 | 1.125 | 1.0 | | | Liquid at 0° C. | 0.14 | 139 |
| 10C | 100 | 0.25 | 2.0 | | | Liquid at 0° C. | 0.09 | 121 |
| 11A | 0 | 2.25 | 0.2 | 3-MBPy | 0.8M | Liquid at −5° C. | 0.065 | 130 |
| 11B | 50 | 1.125 | 1.0 | | | Liquid at −5° C. | 0.080 | 149 |
| 11C | 100 | 0.25 | 2.0 | | | Liquid at −5° C. | 0.028 | 131 |
| 12A | 0 | 2.25 | 0.2 | 3-MPePy | 0.8M | Liquid at 0° C. | 0.02 | 131 |
| 12B | 50 | 1.125 | 1.0 | | | Liquid at 0° C. | 0.36 | 140 |
| 12C | 100 | 0.25 | 2.0 | | | Liquid at 0° C. | 0.07 | 122 |

In the second sub-set of Examples, mixtures consisting of two different 1-alkyl-3-methyl-pyridinium bromides were tested as complexing agents for zinc/bromine cells. The results are tabulated in Table 2.

TABLE 2

| Ex. | % SOC | $ZnBr_2$(M) | $Br_2$, M | additive | [additive] [M] | Physical state of polybromide complex | % $Br_2$, aq. | Con, mS/cm |
|---|---|---|---|---|---|---|---|---|
| 13A | 0 | 2.25 | 0.2 | 3-MBPy/ | 0.8M | Liquid at −5° C. | 0.051 | 122 |
| 13B | 50 | 1.125 | 1.0 | 3-MEPy | | Liquid at −5° C. | 0.070 | 143 |
| 13C | 100 | 0.25 | 2.0 | 3:1 | | Liquid at −5° C. | 0.027 | 129 |

In the third sub-set of Examples, mixtures consisting of one 1-alkyl-3-methyl-pyridinium bromide and one 1-alkyl-2-methyl-pyridinium bromide were tested as complexing agents for zinc/bromine cells. The results are tabulated in Table 3.

TABLE 3

| Ex. | % SOC | $ZnBr_2$(M) | $Br_2$, M | additive | [additive] [M] | Physical state of polybromide complex | % $Br_2$, aq. | Con, mS/cm |
|---|---|---|---|---|---|---|---|---|
| 14A | 0 | 2.25 | 0.2 | 3-MBPy/ | 0.8M | Liquid at −5° C. | 0.064 | 120 |
| 14B | 50 | 1.125 | 1.0 | 2-MEPy | | Liquid at −5° C. | 0.088 | 143 |
| 14C | 100 | 0.25 | 2.0 | 3:1 | | Liquid at −5° C. | 0.020 | 124 |

In the fourth sub-set of Examples, the additive tested was a mixture consisting of 1-alkyl-3-methyl-pyridinium bromide together with a compound of Formula (I), i.e., N-alkyl pyridinium bromide. The results are tabulated in Table 4.

TABLE 4

| Ex. | % SOC | $ZnBr_2$(M) | $Br_2$, M | additive | [additive] [M] | Physical state of polybromide complex | % $Br_2$, aq. | Con, mS/cm |
|---|---|---|---|---|---|---|---|---|
| 15A | 0 | 2.25 | 0.2 | 3-MBPy/ | 0.8M | Liquid at −5° C. | 0.056 | 115 |
| 15B | 50 | 1.125 | 1.0 | EPy | | Liquid at −5° C. | 0.077 | 138 |
| 15C | 100 | 0.25 | 2.0 | 3:1 | | Liquid at −5° C. | 0.025 | 128 |

In the fifth sub-set of Examples, the additive tested was a mixture consisting of 1-alkyl-3-methyl-pyridinium bromides together with a compound of Formula (I), i.e., N-alkyl pyridinium bromide and 1-alkyl-2-methyl pyridinium bromide, and the property measured was the viscosity of each of the separate phases. The results are tabulated in Table 5 (vis. is the abbreviation of viscosity).

TABLE 5

| Ex. | % SOC | $ZnBr_2$(M) | $Br_2$, M | additive | [additive] [M] | % $Br_2$, aq. | Vis. of aqueous phase (cP) | Vis. of organic phase (cP) | Volumetric ratio aqu./org phases |
|---|---|---|---|---|---|---|---|---|---|
| 16A | 0 | 2.25 | 0.2 | 3-MBPy/ | 0.8M | 0.134 | 23.9 | 56.9 | 4.3 |
| 16B | 50 | 1.125 | 1.0 | EPy | | 0.251 | 17.2 | 18.7 | 2.6 |
| 16C | 100 | 0.25 | 2.0 | (1:1) | | 0.591 | 12.3 | 12.1 | 2.0 |
| 17A | 0 | 2.25 | 0.2 | 3-MBPy/ | 0.8M | 0.093 | 23.3 | 57.8 | 2.9 |
| 17B | 50 | 1.125 | 1.0 | 2-MEPy | | 0.183 | 15.8 | 21.7 | 2.3 |
| 17C | 100 | 0.25 | 2.0 | (1:1) | | 0.702 | 11.9 | 12.8 | 2.6 |

In the sixth sub-set of Examples, the additive tested was a mixture consisting of 1-alkyl-3-methyl-pyridinium bromide together with a compound of Formula (III), i.e., 1-n-butyl-3-methyl imidazolium bromide (BMIBr). The results are tabulated in Table 6.

TABLE 6

| Ex. | % SOC | $ZnBr_2$(M) | $Br_2$, M | additive | [additive] [M] | Physical state of polybromide complex | % $Br_2$, aq. | Con, mS/cm |
|---|---|---|---|---|---|---|---|---|
| 18A | 0 | 2.25 | 0.2 | BMIBr/ | 0.8M | Liquid at −5° C. | 0.105 | 114 |
| 18B | 50 | 1.125 | 1.0 | 3-MEPy | | Liquid at −5° C. | 0.100 | 140 |
| 18C | 100 | 0.25 | 2.0 | 3:1 | | Liquid at −5° C. | 0.178 | 140 |
| 19A | 0 | 2.25 | 0.2 | BMIBr/ | 0.8M | Liquid at −5° C. | 0.075 | 111 |
| 19B | 50 | 1.125 | 1.0 | 3-MEPy | | Liquid at −5° C. | 0.075 | 137 |
| 19C | 100 | 0.25 | 2.0 | 1:1 | | Liquid at −5° C. | 0.080 | 139 |

Examples 20-21

Figure 2:
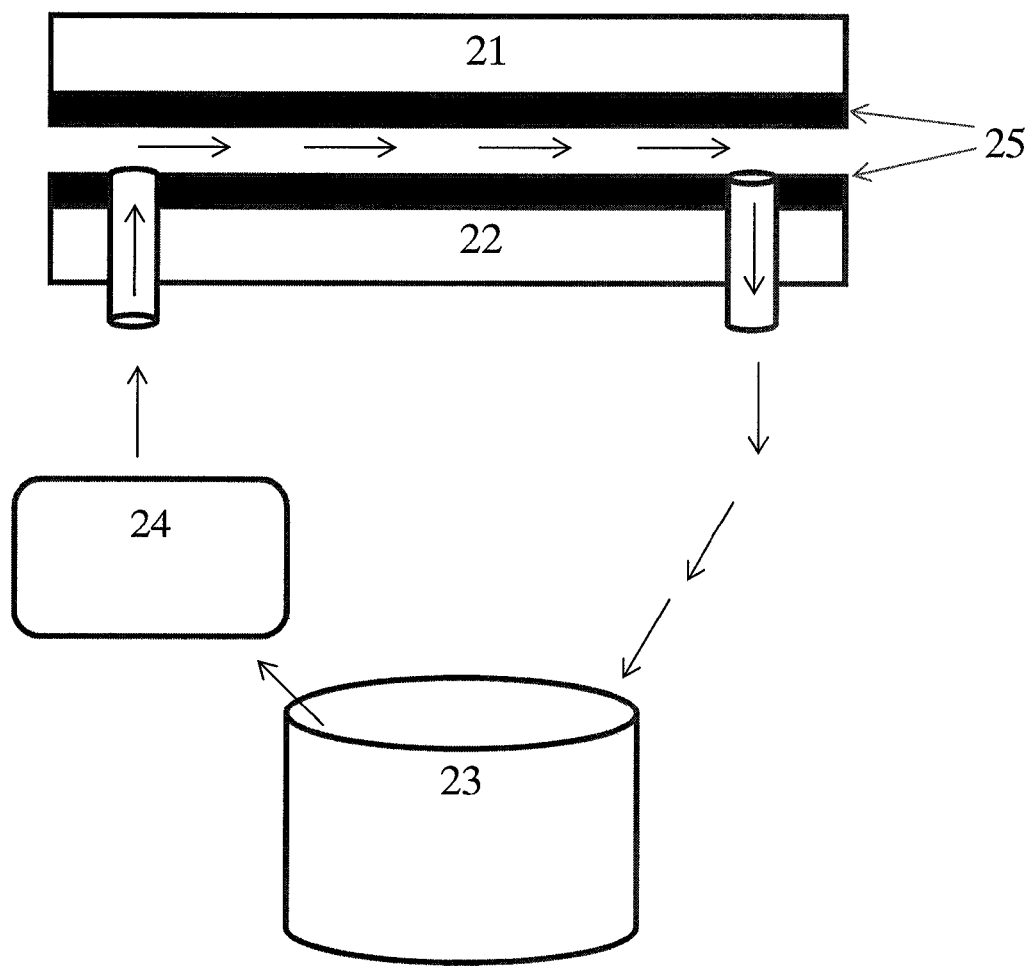

An experimental set-up which is schematically illustrated in FIG. 2 was used to evaluate the effect of the presence of various bromine complexing agents on the efficacy of the operation of zinc/bromine membraneless cell. A characteristic property of the cell which was chosen for a quantitative study is the efficiency of zinc plating formed onto the anode surface, when the cell was charged at current density of 60 mA/cm$^2$.

During charge, zinc metal is increasingly formed on the anode and elemental bromine is increasingly generated in the electrolyte. In the set of experiments described below, various bromine-complexing agents were added to zinc bromide aqueous electrolyte which was recirculated in a membraneless electrochemical cell configuration during charge, and the bromine-complexing agents were tested for their ability to capture and hold the elemental bromine in the form of water-immiscible phase, minimizing the dissolution of elemental bromine in the aqueous phase of the electrolyte and correspondingly decreasing the direct chemical oxidation of the zinc by elemental bromine present in the aqueous phase. Thus, in membraneless cells, in the absence of physical membrane separating between the zinc and bromine electrodes, the plating efficiency of the zinc critically depends on the efficacy of the bromine-complexing agent.

Experimental Set-Up

Referring to FIG. 2, the experimental set-up comprises a pair of graphite electrodes 21 and 22 which serve as zinc and bromine electrodes, respectively. The electrode plates are made of compressed graphite particles, are rectangular in shape and are about 5 mm thick. The electrodes are mounted horizontally, in parallel with one another, and are spaced 2 mm apart. As shown in FIG. 2, the zinc electrode is placed on top of the bromine electrode. It is noted that no membrane is interposed in the space between the electrodes.

Viton® gaskets 25 are applied onto the sides of the electrodes which face each other, i.e., the lower and upper faces of electrodes 21 and 22, respectively, are covered with the gasket, except for a central region which is left exposed on each of said electrodes faces. The non-coated central regions of the electrodes are hence available for the electrochemical reactions. The electrochemically-reactive central regions on the lower and upper faces of electrodes 21 and 22, respectively, coincide with one another with respect to position, geometric shape and size. Each of the two opposed electrochemically-reactive central regions has the shape of a square with an area of 10 cm$^2$.

A flow distributor provided in the form of a Teflon® frame corresponding in shape and size to the rectangular electrodes 21 and 22 is positioned in the space between said electrodes, such that the central open area of the frame coincides with the non-coated active regions of the electrodes with respect to position, geometric shape and size. FIG. 3 provides a top view of the relevant elements, i.e., the electrode plates 21, 22, Viton® gasket 25 and Teflon® flow distributor 26 which were used in the experimental set-up of FIG. 2. The electrode plates are perforated to allow the access and exit of electrolyte flow.

The Compositions of the Tested Solutions

The aqueous electrolyte solutions that were tested contain zinc bromide, elemental bromine and zinc chloride, the latter at a constant concentration of 0.4M. It should be noted that the electrolyte solutions prepared fall into two groups, A and B, which differ from one another in respect to the initial concentrations of the zinc bromide and elemental bromine:

[ZnBr$_2$]=~1.7 M, [Br$_2$]=0.5 wt %         Group A

[ZnBr$_2$]=~1.0 M, [Br$_2$]=~1.0M.           Group B

The composition of solutions of group A corresponds to a state of charge of 0%, i.e., it represents a composition of an electrolyte solution at the beginning of the charging process (a small amount of elemental bromine is present to avoid over potential). The composition of the solutions of group B is representative of a state of charge of 60%. During the experiments, while the electrolysis is in progress, the composition of the solutions gradually varies, with the concentrations of zinc bromide and elemental bromine decreasing and increasing, respectively, such that the final compositions of the solutions of groups A and B match states of charges of 25%-30% and -90%, respectively. Thus, the activity of the bromine-complexing agents (BCA) was investigated at two distinct "windows" of the cell charge: from 0 to 30% SOC (Group A), and from 60 to 90% SOC (Group B). The BCA tested were either 3-MBPy alone or a mixture of 3-MBPy and 3-MEPy (1:1 molar mixture).

The Experiments

All the experiments were carried out at room temperature, with the cell being charged at current density of 60 mA/cm2.

Each experiment is run as follows. The electrolyte solution under study is held in a reservoir 23. The electrolyte volume is 90-100 ml (110-130 g). Peristaltic pump 24, operating at 30 rpm up to 100 rpm, drives the electrolyte solution through the cell, causing the solution to flow in the space between electrodes 21 and 22. The flow path of the electrolyte is schematically indicated by means of arrows in FIG. 2. The electrolyte solution is drawn from the upper (aqueous) part of the electrolyte volume and returned to the bottom of reservoir 23, where the dense (organic) phase accumulates. The experiments lasted about 4.5-5.5 hours. At the end of the experiment, the cell was opened and washed in water and NaHSO$_3$ solution. The anode with Zn deposited thereon was washed several times with deionized water, dried and carefully removed and weighted, to determine the mass of zinc formed through the electrolysis. Plating efficiency was calculated as follows:

$$\text{Plating efficiency} = \frac{M}{\left(\frac{I*t}{F}\right)*\left(\frac{M_w}{z}\right)} * 100$$

M—mass of zinc deposited on the electrode
I—electrical current (0.6 A)
t—time during which the current passed through the cell (sec)
F—Faraday constant (96485 C/mol)
Mw—molecular weight (g/mol)
z—metal valence (2)

The details and the results are tabulated in Table 7.

TABLE 7

| Ex. | t (h) | % SOC | ZnBr$_2$ (M) | Br$_2$ (M) | BCA Additive | [BCA] M | Plating efficiency % |
|---|---|---|---|---|---|---|---|
| 20A | 5.5 | 0→30 | ~1.7→1.2 | 0.2-0.6 | 3-MBPy | 0.8M | 94% |
| 20B | 5.0 | 60→92 | ~1.0→0.14 | 1.0→1.6 | | | 97% |
| 21A | 4.5 | 0→25 | ~1.7→1.28 | 0.2-0.5 | 3-MBPy + 3-MEPy | 0.8M | 89% |

The results in Table 7 demonstrate the efficacy of 3-MBPy and mixtures thereof in minimizing the amount of free bromine in the aqueous phase, thereby lessening the direct reaction between bromine in the electrolyte and the plated Zn (i.e., the undesired self-discharge), as shown by the high level of plating efficiency maintained in the presence of said additive.

Examples 22-23

Zinc bromide electrolyte Solutions which Contain N-methyl-N-isooctyl pyrrolidinium bromide To demonstrate the effect of mixtures of N-methyl-N-isooctyl pyrrolidinium bromide and 1-butyl 3-methyl imidazolium bromide together (at molar ratios of 1:3 and 1:1), 24 ml samples were prepared with electrolyte compositions corresponding to three distinct states of charge (SOC) defined by the concentrations of zinc bromide and elemental bromine. In addition to zinc bromide and elemental bromine (which were present in the samples in suitable amounts as set out in Table 8 below in order to match the state of charge investigated), each sample also contained zinc chloride and potassium chloride at constant concentrations of 0.5M and 1.0M, respectively. The samples were stored at 25° C. for 24-48 hours after preparation before any measurement was conducted. The samples were tested for one or more of the following properties: the temperature at which a solid phase is formed in the electrolyte, free bromine concentration in the aqueous phase and conductivity. The results are set out in Table 8.

TABLE 8

| Ex. | % SOC | ZnBr$_2$(M) | Br$_2$, M | additive | [additive] [M] | Physical state of polybromide complex | % Br$_2$, aq. | Con, mS/cm |
|---|---|---|---|---|---|---|---|---|
| 22A | 0 | 2.25 | 0.2 | BMIBr/MiOP 3:1 | 0.8M | Liquid at −5° C. | <0.001 | 127 |
| 22B | 50 | 1.125 | 1.0 |  |  | Liquid at −5° C. | 0.094 | 145 |
| 22C | 100 | 0.25 | 2.0 |  |  | Liquid at −5° C. | 0.047 | 139 |
| 23A | 0 | 2.25 | 0.2 | BMIBr/MiOP 1:1 | 0.8M | Liquid at −5° C. | <0.001 | 125 |
| 23B | 50 | 1.125 | 1.0 |  |  | Liquid at −5° C. | 0.055 | 148 |
| 23C | 100 | 0.25 | 2.0 |  |  | Liquid at −5° C. | 0.062 | 145 |

Table 8 illustrates that the mixed bromine-containing complex is highly effective, as it did not undergo solidification even at a temperature as low as −5° C., the amount of bromine measured in the aqueous phase is very low and the electrolyte solution exhibits good conductivity.

Examples 24 (Comparative) and 25 (of the Invention)

Zinc bromide electrolyte Solutions which Contain N-methyl-N-ethyl pyrrolidinium bromide and N-methyl-N-butyl pyrrolidinium bromide The procedures set forth in previous examples were repeated, but this time the complexing agent used was N-methyl-N-ethyl pyrrolidinium bromide (MEP; Example 24) and N-methyl-N-butyl pyrrolidinium bromide (MBP; Example 25). The results are given in Table 9.

TABLE 9

| Ex. | % SOC | ZnBr$_2$(M) | Br$_2$, M | additive | [additive] [M] | Physical state of polybromide complex | % Br$_2$, aq. | Con, mS/cm |
|---|---|---|---|---|---|---|---|---|
| 24A | 0 | 2.25 | 0.2 | MEP | 0.8M | Liquid at 0° C. | 0.44 | 88 |
| 24B | 50 | 1.125 | 1.0 |  |  | Soild at 0° C. | 0.60 | 95 |
| 24C | 100 | 0.25 | 2.0 |  |  | Soild at 5° C. | 0.98 | 90 |
| 25A | 0 | 2.25 | 0.2 | MBP | 0.8M | Liquid at −5° C. | 0.07 | 68 |
| 25B | 50 | 1.125 | 1.0 |  |  | Liquid at −5° C. | 0.12 | 111 |
| 25C | 100 | 0.25 | 2.0 |  |  | Liquid at −5° C. | 0.65 | 90 |

Table 9 illustrates that the bromine-containing complex based on MEP solidifies already at 5° C. and the conductivity of the electrolyte solution is relatively low, clearly indicating the inferiority of MEP in comparison to the additives of the invention. The amount of 'free' bromine in the aqueous phase is relatively high.

Preparations 1-3

Preparation of N-ethyl pyridinium bromide (EPy)

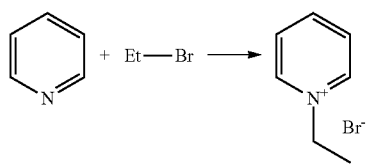

1) Preparation of EPy in an Aqueous Medium:

A stirred pressure reactor was equipped with a thermocouple well and a dosing pump. The reactor was charged with pyridine (450 g) and de-ionized water (DIW) (330 mL), sealed and heated to 95° C. Ethyl bromide (600 g) was continuously added during 1 hour; afterwards heating was continued for additional 1 hour. The reactor was cooled to ambient temperature, the pressure was released and distillation apparatus installed. The reaction mass was diluted with DIW (200 mL) and distilled under vacuum until 200 mL of distillate were collected. Final product: 1340 g; 72% w (argentometric titration); yield, 93%.

2) Preparation of EPy in Aqueous Medium:

A stirred pressure reactor was equipped with a thermocouple well and a dosing pump. The reactor was charged with pyridine (475 g) and de-ionized water (DIW) (282 mL), sealed and heated to 95° C. Ethyl bromide (674 g) was continuously added during 1 hour; afterwards heating was continued for additional 1 hour. The reactor was cooled to ambient temperature, the pressure was released and distillation apparatus installed. The reaction mass was diluted with DIW (200 mL) and distilled under vacuum until 200 mL of distillate were collected. Final product: 1384 g; 77% w (argentometric titration); yield, 95%.

3) Preparation of EPy without a Solvent

A stirred pressure reactor was equipped with a thermocouple well and a dosing pump. The reactor was charged with pyridine (475 g), sealed and heated to 90° C. Ethyl bromide (667 g) was continuously added during 1 hour; afterwards heating was continued for additional 1 hour. The reactor was cooled to ambient temperature, the pressure was released and distillation apparatus installed. Initial distillation was applied under vacuum for 15 minutes. The reaction mass was diluted with DIW (300 mL) and further distilled under vacuum until 150 mL of distillate were collected. Final product: 1230 g; 88% w (argentometric titration); yield, 96%.

Preparations 4-6

Preparation of N-ethyl-2-methyl pyridinium bromide (2-MEPy)

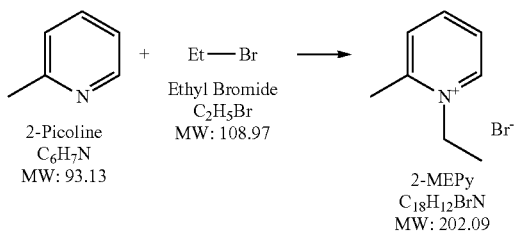

4) Preparation of 2-MEPy in an Aqueous Medium

A pressure reactor was equipped with a mechanical stirrer with a magnetic relay and a thermocouple well. The reactor was charged with 2-picoline (101.3 g) and de-ionized water (DIW) (20 mL), sealed and the mixture was heated to 92° C. Ethyl bromide (97.9 g) was slowly added during 3 hours, at 92-100° C. The mixture was heated at 94-100° C. for additional 2 hours, then cooled, and the pressure was released. The crude solution was diluted with DIW (24 mL) and excess 2-picoline was distilled-off as aqueous azeotrope, under reduced pressure. Finally, the residue was diluted with DIW. Final product: 251 g; 66.1 weight % (argentometric titration); yield, 91.5%.

5) Preparation of 2-MEPy in Acetonitrile as a Solvent

A pressure reactor was equipped with a mechanical stirrer with a magnetic relay and a thermocouple well. The reactor was charged with 2-picoline (57.9 g), ethyl bromide (69 g) and acetonitrile (69 g). The reactor was sealed and the mixture heated to 97° C. Heating at 97° C. was continued for 6 hours. Distillation of the solvent was controlled by the upper valve of the reactor followed by vacuum distillation (without cooling). DIW (31 mL) was added to dissolve the crude mixture and vacuum was applied to remove residual acetonitrile. Finally, the solution was diluted with DIW (10.5 g). Final product: 149 g; 80.0 weight % (argentometric titration); yield, 95%.

6) Preparation of 2-MEPy with Excess of Ethyl Bromide

A pressure reactor was equipped with a mechanical stirrer with a magnetic relay and a thermocouple well. The reactor was charged with 2-picoline (95 g) and ethyl bromide (145 g). The reactor was sealed and the mixture heated to 97° C. Heating at 97° C. was continued for 18 hours. Distillation of excess ethyl bromide was controlled by the upper valve of the reactor followed by vacuum distillation (without cooling). Finally, the solution was diluted with DIW (47 g). Final product: 250 g; 79.3 weight % (argentometric titration); yield, 96%.

Preparations 7-8

Preparation of N-methyl-N-isooctyl pyrrolidinium bromide (MiOP)

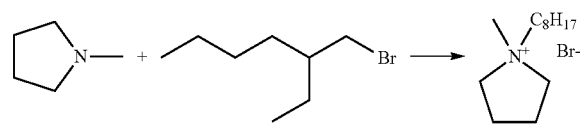

7) Preparation of MiOP in Acetonitrile as a Solvent:

A four neck round bottom flask was equipped with a mechanical stirrer, a condenser, a thermocouple well and a dropping funnel. The flask was purged with nitrogen during the whole procedure. The flask was charged with 1-methylpyrrolidine (49 g) and acetonitrile (63 g) and heated to 80° C. 2-Ethylhexylbromide (100 g) was added drop-wise during 1.5 hours. The reaction mixture was heated at 80-104° C. for 3 hours. The mixture was cooled and the volatiles evaporated in a rotavapor. DIW (100 mL) and evaporation was applied twice. Finally, DIW was added to correct dilution. Final product, 184 g, 63.1 weight % (argentometric titration); yield, 80.5%.

8) Preparation of MiOP without a Solvent:

A four neck round bottom flask was equipped with a mechanical stirrer, a condenser, a thermocouple well and a dropping funnel. The flask was purged with nitrogen during the whole procedure. The flask was charged with 1-methylpyrrolidine (681 g) and 2-ethylhexylbromide (1400 g). The reaction mixture was heated to 100° C. during 2 hours and kept at that temperature for 4 hours. DIW (1 L) was added, the mixture was cooled and the volatiles evaporated in a rotavapor (900 mL distillate were collected). Additional DIW (200 mL) was added and the mixture was re-evaporated. DIW was added to correct dilution. Final product, 2551 g, 77.8 weight % (argentometric titration); yield, 98.4%.

The entitled compound was identified as follows: M.P. by DSC: 85.6° C. (peak). $^1$H NMR: (D$_2$O, TMS) δ ppm 3.56-3.42 (4H, m), 3.29 (1H, dd, J$_1$=14 Hz, J$_2$=5 Hz), 3.25 (1H, dd, J$_1$=14 Hz, J$_2$=5 Hz), 3.03 (3H, s), 2.24-2.15 (4H, m), 1.90-1.82 (1H, m), 1.52-1.37 (4H, m), 1.33-1.25 (4H, m), 0.89 (3H, t, J=7.3 Hz), 0.87 (3H, t, J=7.1 Hz).

The invention claimed is:
1. An electrolyte solution suitable for use in bromine-generating electrochemical cells, comprising an aqueous solution of zinc bromide and a liquid complex composed of at least one 1-alkyl-3-methyl-pyridinium halide combined with one or more bromine molecules, wherein said alkyl at position 1 is a C3-C10 alkyl group which may be either straight-chain or branched, wherein said electrolyte solution is configured for circulation in a zinc/bromine cell.

2. The electrolyte solution according to claim 1, wherein the C3-C10 alkyl group is selected from the group consisting of n-propyl, n-butyl, n-pentyl and n-hexyl.

3. The electrolyte solution according to claim 2, comprising 1-n-butyl-3-methyl-pyridinium bromide.

4. The electrolyte solution according to claim 3, further comprising at least one compound selected from the group consisting of 1-n-propyl-3-methyl-pyridinium bromide, 1-n-pentyl-3-methyl-pyridinium bromide and 1-n-hexyl-3-methyl-pyridinium bromide.

5. The electrolyte solution according to claim 1, wherein the electrolyte solution further comprises one or more compounds of Formulas I, II or III:

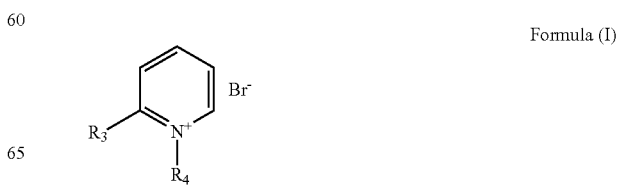

Formula (I)

-continued

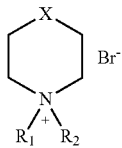

Formula (II)

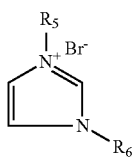

(Formula (III))

wherein:

in Formula (I), $R_3$ is hydrogen or alkyl group and $R_4$ is independently an alkyl group;

in Formula (II), X is null, —$CH_2$— or —O—, and $R_1$ and $R_2$ are independently alkyl groups, with at least one of $R^1$ and $R^2$ being an alkyl group comprising not less than three carbon atoms; and in Formula (III), $R_5$ and $R_6$ are independently an alkyl group.

6. The electrolyte solution according to claim 5, wherein the compound of Formula (I) is selected from the group consisting of N-alkyl pyridinium bromide and 1-alkyl-2-methyl pyridinium bromide; the compound of Formula (II) is selected from the group consisting of N-methyl-N-alkyl pyrrolidinium bromide, wherein said alkyl group attached to the pyrrolidinium ring comprises not less than four carbon atoms; and the compound of Formula (III) is 1-alkyl-3-methyl imidazolium bromide.

7. The electrolyte solution according to claim 6, wherein the compound of Formula (I) is selected from the group consisting of N-ethyl pyridinium bromide and 1-ethyl-2-methyl pyridinium bromide; the compound of Formula (II) is selected from the group consisting of N-methyl-N-butyl pyrrolidinium bromide, N-methyl-N-hexyl pyrrolidinium bromide and N-methyl-N-isooctyl pyrrolidinium bromide; and the compound of Formula (III) is 1-n-butyl-3-methyl imidazolium bromide.

8. The electrolyte solution according to claim 1, wherein the liquid complex does not solidify at a temperature above 0° C.

9. A method of operating a bromine-generating electrochemical cell which is a zinc/bromine cell, comprising adding to the electrolyte of said cell at least one 1-alkyl-3-methyl-pyridinium halide, wherein the alkyl at position 1 is a C3-C10 alkyl group, which may be either straight-chain or branched; and charging and/or discharging said cell.

10. The method according to claim 9, which further comprises adding to the electrolyte a compound of Formulas (I), (II) or (III):

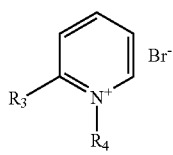

Formula (I)

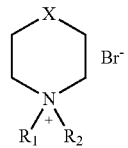

Formula (II)

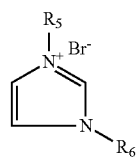

(Formula (III))

wherein:

in Formula (I), $R_3$ is hydrogen or alkyl group and $R_4$ is independently an alkyl group;

in Formula (II), X is null, —$CH_2$— or —O—, and $R_1$ and $R_2$ are independently alkyl groups, with at least one of $R^1$ and $R^2$ being an alkyl group comprising not less than three carbon atoms; and in Formula (III), $R_5$ and $R_6$ are independently an alkyl group.

11. The method according to claim 9, comprising forming a liquid complex composed of at least one 1-alkyl-3-methyl-pyridinium bromide combined with one or more bromine molecules, wherein said alkyl at position 1 is C3-C10 alkyl group which may be either straight-chain or branched, wherein the liquid complex does not solidify at a temperature above 0° C.

12. A process for preparing an aqueous solution of one or more 1-alkyl-3-methyl-pyridinium bromide, wherein the alkyl at position 1 is C3-C10 alkyl group, which may be either straight-chain or branched, comprising reacting 3-picoline and one or more bromoalkanes in a reaction vessel at a temperature above the melting point of the reaction mixture, in the absence of a solvent, combining the reaction product with water, wherein said reaction product consists essentially of 1-alkyl-3-methyl-pyridinium bromide in a liquid form, and recovering an aqueous solution of said 1-alkyl-3-methyl-pyridinium bromide.

13. The process according to claim 12, which does not involve the formation, isolation and purification of the 1-alkyl-3-methyl-pyridinium bromide in a solid form.

14. The process according to claim 13, wherein the solvent-free reaction mixture is heated to a temperature of not less than 70° C., maintaining the progressively formed 1-alkyl-3-methyl-pyridinium bromide in a liquid form and providing a stirrable reaction mass, and combining the liquid 1-alkyl-3-methyl-pyridinium bromide directly with water to form a clear aqueous solution.

15. A concentrated aqueous solution comprising at least one 1-alkyl-3-methyl-pyridinium bromide, wherein the alkyl at position 1 is C3-C10 alkyl group, which may be either straight-chain or branched, wherein the concentration of the solution is from 60 wt % to 90 wt %.

16. The concentrated aqueous solution according to claim 15, comprising at least one 1-alkyl-3-methyl-pyridinium bromide selected from the group consisting of 1-n-propyl-3-methyl-pyridinium bromide, 1-n-butyl-3-methyl-pyridinium bromide, 1-n-pentyl-3-methyl-pyridinium bromide and 1-n-hexyl-3-methyl-pyridinium bromide.

17. The concentrated aqueous solution according to claim 16, further comprising 1-ethyl-3-methyl pyridinium bromide.

18. The concentrated aqueous solution according to claim 15, wherein the 1-alkyl-3-methyl-pyridinium bromide was isolated in a non-solid form.

* * * * *